United States Patent [19]

Woo et al.

[11] Patent Number: 5,631,236

[45] Date of Patent: May 20, 1997

[54] GENE THERAPY FOR SOLID TUMORS, USING A DNA SEQUENCE ENCODING HSV-TK OR VZV-TK

[75] Inventors: Savio L. C. Woo; Shu-Hsia Chen, both of Houston, Tex.

[73] Assignee: Baylor College of Medicine, Houston, Tex.

[21] Appl. No.: 112,745

[22] Filed: Aug. 26, 1993

[51] Int. Cl.$^6$ .................. A61K 48/00; A01N 63/00; C12N 5/00
[52] U.S. Cl. .................. 514/44; 424/93.6; 435/320.1
[58] Field of Search .................. 514/44

[56] References Cited

PUBLICATIONS

Stratford–Perricaudet, et al.; Evaluation of the Transfer and Expression in Mice of an Enzyme–Encoding Gene Using a Human Adenovirus Vector; Human Gene Therapy; 1:241–256 (1990).

O'Malley, et al.; Adenovirus–mediated Gene Therapy for Human Head and Neck Squamous Cell Cancer in a Nude Mouse Model; Cancer Research; 55:1080–1085 (1995).

Chen, et al.; Combination gene therapy for liver metastasis of colon carcinoma in vivo; Proc. Natl. Acad. Sci. USA; 92:2577–2581 (1955).

Bonnekoh, et al.; Inhibition of Melanoma Growth by Adenoviral–Mediated HSV Thymidine Kinase Gene Transfer In Vivo; J. Invest. Dermatol.; 104:313–317 (1995).

Chen, et al.; Gene therapy for brain tumors: Regression of experimental gliomas by adenovirus–mediated gene transfer in vivo; Proc. Natl. Acad. Sci. USA; 91:3054–3057 (1994).

Smythe, et al.; Successful Adenovirus–Mediated Gene Transfer in an In Vivo Model of Human Malignant Mesothelioma; Ann. Thorac. Surg.; 57:1395–401 (1994).

Perez–Cruet, et al.; Adenovirus–Mediated Gene Therapy of Experimental Gliomas; J. Neurosci. Res.; 39:506–511 (1994).

Caruso; et al.; Regression of established macroscopic liver metastases after in situ transduction of a suicide gene; Proc. Natl. Acad. Sci. USA; 90:7024–7028 (1993).

Gray, et al.; Antisense DNA Inhibition of Tumor Growth Induced by c–Ha–ras Oncogene in Nude Mice; Cancer Res. 53:577–80 (1993).

Fujiwara, et al.; Induction of Chemosensitivity in Human Lung Cancer Cells in Vivo by Adenovirus–mediated Transfer of the Wild–Type p53 Gene; Cancer Res. 54:2287–91 (1994).

Ezzeddine, et al.; Selective Killing of Glioma Cells in Culture and in Vivo by Retrovirus Transfer of the Herpes Simplex Virus Thymidine Kinase Gene; The New Biologist 6:608–14 (1991).

Hann, et al.; Antitumor Effect of Deferoxamine on Human Hepatocellular Carcinoma Growing in Athymic Nude Mice; Cancer 8:2051–56 (1992).

Pantazis, et al.; Camptothecin Derivatives Induce Regression of Human Ovarian Carcinomas Grown in Nude Mice and Distinguish Between Non–Tumorigenic and Tumoringenic Cells In Vitro; Int. J. Cancer 53:863–71 (1993).

Wakeling, et al.; A Potent Specific Pure Antiestrogen with Clinical Potential; Cancer Res. 51:3867–73 (1991).

Pietras, et al.; Antibody to HER–2/neu receptor blocks DNA repair after cisplatin in human breast and ovarian cancer cells; Oncogene 9:1829–38 (1994).

Ogura; Implantation of Genetically Manipulated Fibroblasts into Mice as Antitumor α–Interferon Therapy; Cancer Res. 50:5102–06 (1990).

Gastl, et al.; Retroviral Vector–mediated Lymphokine Gene Transfer into Human Renal Cancer Cells; Cancer Res. 52:6229–36 (1992).

Shin (1979) Meth. Enzmol. LVIII, 370–379.

Rosenfeld et al (1991) Science 252, 431–434.

Culver et al (1992) Science 256, 1550–1552.

*Primary Examiner*—Jacqueline M. Stone
*Assistant Examiner*—Deborah Crouch
*Attorney, Agent, or Firm*—Fulbright & Jaworski LLP

[57] ABSTRACT

The present invention provides a novel method of treating localized solid tumors and papilloma in an individual. The method comprises introducing a recombinant adenoviral vector containing the herpes simplex virus-thymidine kinase gene. Subsequently, a prodrug, such as the drug ganciclovir, is administered to the individual. The methods of the present invention may be used to treat several different types of cancers and papillomas, including colon carcinoma, prostate cancer, breast cancer, lung cancer, melanoma, hepatoma, brain and head and neck cancer.

6 Claims, 16 Drawing Sheets

GENE THERAPY FOR SOLID TUMORS, USING A DNA SEQUENCE ENCODING HSV-TK OR VZV-TK

BACKGROUND OF THE INVENTION

1. Field of the Invention

The present invention relates generally to field of gene therapy. More particularly, the present invention relates to a novel gene therapy method of treating solid tumors, papillomas and warts with gene therapy using an adenoviral vector.

2. Description of the Related Art

Direct introduction of therapeutic genes into malignant cells in vivo can provide an effective treatment of localized tumors. Several novel treatment modalities have recently been attempted. For example, one treatment involves the delivery of normal tumor suppressor genes and/or inhibitors of activated oncogenes into tumor cells. A second treatment involves the enhancement of immunogeneity of tumor cells in vivo by the introduction of cytokine genes. A third treatment involves the introduction of genes that encode enzymes capable of conferring to the tumor cells sensitivity to chemotherapeutic agents. The herpes simplex virus-thymidine kinase (HSV-TK) gene can specifically convert a nucleoside analog (ganciclovir) into a toxic intermediate and cause death in dividing cells. It has recently been reported by Culver et.al. (Science 256:1550–1552, 1992) that after delivery of the HSV-TK gene by retroviral transduction, subsequent ganciclovir treatment effectively caused brain tumor regression in laboratory animals. An attractive feature of this treatment modality for localized tumors is the so called "by-stander" effect. In the "by-stander" effect, the HSV-TK expressing tumor cells prevent the growth of adjacent non-transduced tumor cells in the presence of ganciclovir. Thus, not every tumor cell has to express HSV-TK for effective cancer treatment.

The HSV-TK retrovirus used by Culver et al., however, was limited by low viral titer. Moreover, effective treatment of brain tumors necessitated the inoculation into animals of virus-producing cells rather than the viral isolate itself. The prior art remains deficient in the lack of an efficient gene therapy technique for the treatment of solid tumors.

SUMMARY OF THE INVENTION

An object of the present invention is a novel method of gene therapy in humans and animals.

An additional object of the present invention is a method of treating cancer by introducing an adenoviral vector encoding a protein capable of enzymatically converting a prodrug, i.e., a non-toxic compound into a toxic compound.

Thus, in accomplishing the foregoing objects there is provided in accordance with one aspect of the present invention a method of treating a solid tumor, papilloma or warts in an animal or human, comprising steps of introducing an adenoviral vector directly into solid tumor, that vector comprised of the following elements linked sequentially at appropriate distance for functional expression: a promoter; a 5' mRNA leader sequence; an initiation site; a nucleic acid cassette containing the sequence to be expressed; a 3' untranslated region; and a polyadenylation signal; and administering a prodrug to animal or human, wherein prodrug is converted in vivo in to a toxic compound.

Other and further objects, features and advantages will be apparent from the following description of the presently preferred embodiments of the invention which are given for the purpose of disclosure when taken in conjunction with the accompanying drawings.

Figure 1:
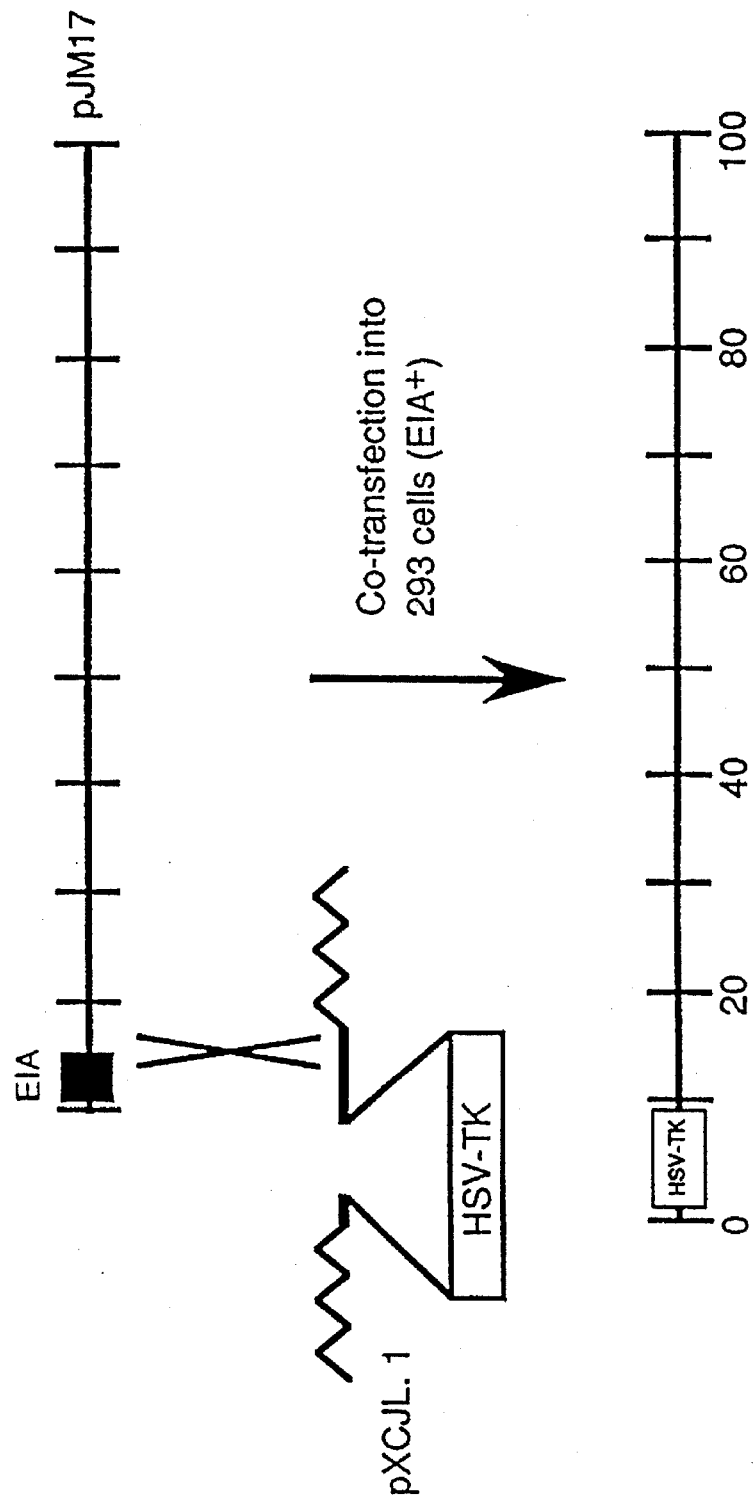
FIG. 1 shows a schematic representation of the construction of recombinant adenoviral vectors containing the herpes simplex virus thymidine kinase (HSV-TK) gene.
Figure 2A:
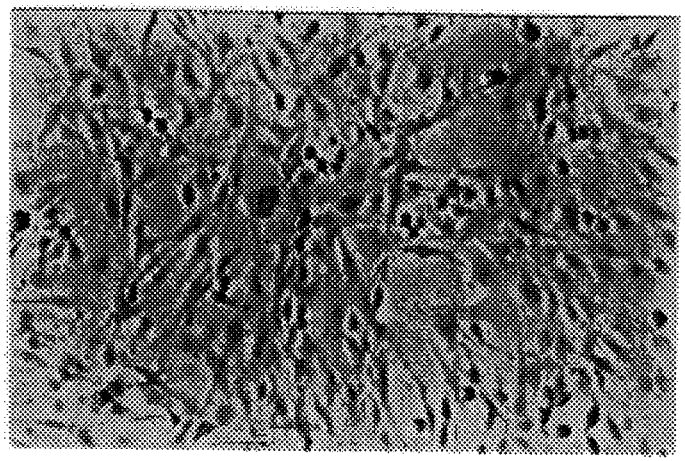
FIG. 2 shows the efficient transduction of C6 glioma cells in vitro using a recombinant adenoviral vector containing the bacterial B-galactosidase gene. Panel A: moi=O; Panel B: moi=125; Panel C: moi=500 and Panel D, moi=2,0000.
Figure 2B:
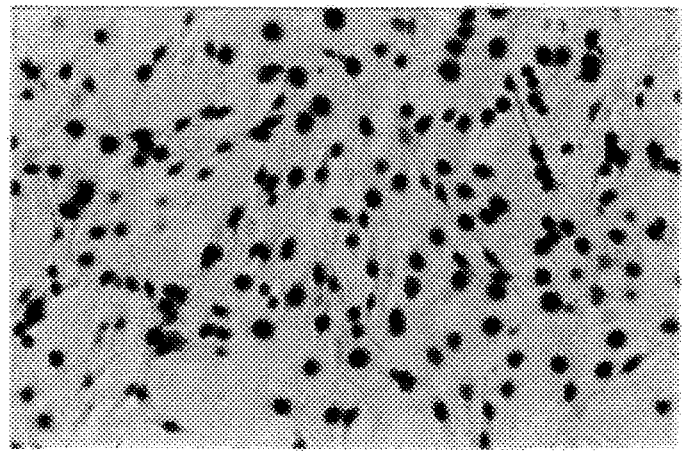
Figure 2C:
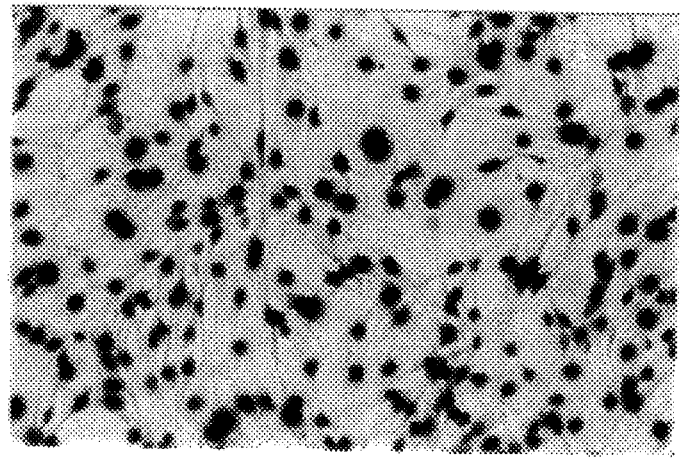
Figure 2D:
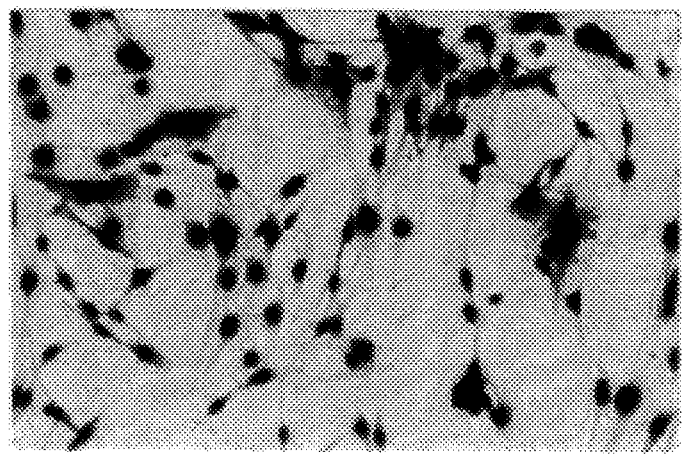

The drawings are not necessarily to scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

The term "vector" as used herein refers to a construction comprised of genetic material designed to direct transformation of a targeted cell. A vector contains multiple genetic elements positionally and sequentially oriented, i.e., operatively linked with other necessary elements such that the nucleic acid in a nucleic acid cassette can be transcribed and when necessary, translated in the transfected cells. In the present invention, the preferred vector comprises the following elements operatively linked for functional expression: a promoter; a 5' mRNA leader sequence; an initiation site; a nucleic acid cassette, containing the sequence to be expressed; a 3' untranslated region; and a polyadenylation signal.

The term "stable transformation" as used herein refers to transformation in which the introduced therapeutic nucleic acid sequence is incorporated into the chromosomes of the whole cell. This leads to apparent stable change or transformation of a given characteristic of a cell.

The term "transformed" as used herein refers to a process for making or introducing a stable change in the characteristics (express phenotype) of a cell by the mechanism of gene transfer whereby DNA or RNA is introduced into a cell in a form where it expresses a specific gene product or alters an expression or affects endogenous gene products. The vector can be introduced into the cell by a variety of methods including microinjection, $CaPO_4$ precipitation, lipofection (liposome fusion), use of a gene gun and DNA vector transporter.

Recombinant adenoviruses containing the HSV-TK gene can be driven by various promoters including that of the cytomegalovirus, Rouse sarcoma virus LTR, murine leukemia virus LTR, simian virus 40 early and late, and endogenous HSV-TK genes. The recombinant adenoviruses are used to efficiently deliver the HSV-TK gene to tumors.

A wide variety of cancer, papillomas and warts can be treated by the same therapeutic strategy. Representative examples include colon carcinoma, prostate cancer, breast cancer, lung cancer, skin cancer, liver cancer, bone cancer, ovary cancer, pancreas cancer, brain cancer, head and neck cancer and other solid tumors. Representative examples of papillomas include squamous cell papilloma, choroid plexus papilloma and laryngeal papilloma. Representative examples of wart conditions include genital warts, plantar warts, epidermodysplasia verruciformis and malignant warts.

The term "nucleic acid cassette" as used herein refers to the genetic material of interest which can express a protein, or a peptide, or RNA. The nucleic acid cassette is operatively linked i.e., positionally and sequentially oriented in a vector, with other necessary elements such that the nucleic acid in the cassette can be transcribed and, when necessary, translated.

The present invention provides a method of treating a localized solid tumor, papilloma or warts in an animal or human, comprising steps of: introducing an adenoviral vector directly into said tumor or papilloma, comprised of the following elements linked sequentially at appropriate distance for functional expression: a promoter; a 5' mRNA leader sequence; an initiation site; a nucleic acid cassette containing the sequence to be expressed; a 3' untranslated region; and a polyadenylation signal; and administering a prodrug to animal or human, wherein prodrug is converted in vivo in to a toxic compound.

Various promoters may be used to drive the vector useful in the method of the present invention. Representative examples of a useful promoter are selected from the group consisting of Rous Sarcoma Virus -Long Terminal Repeat, cytomegalovirus promoter, murine leukemia virus LTR, simian virus 40 early and late, and herpes simplex virus thymidine kinase.

In the method of the present invention, the therapeutic nucleic acid sequence is a nucleic acid coding for a product, wherein product causes cell death by itself or in the presence of other drugs.

A representative example of such a therapeutic nucleic acid is one which codes for thymidine kinase of herpes simplex virus. Additional examples are thymidine kinase of varicella zoster virus and the bacterial gene cytosine deaminase which can convert 5-fiuorocytosine to the highly toxic compound 5-fluorouracil.

The prodrug useful in the methods of the present invention is any that can be converted to a toxic product, i.e. toxic to tumor cells. The prodrug is converted to a toxic product by the gene product of the therapeutic nucleic acid sequence in the vector useful in the method of the present invention. Representative examples of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deambinase.

Ganciclovir may be readily administered by a person having ordinary skill in this art. A person with ordinary skill would readily be able to determine the most appropriate dose and route for the administration of ganciclovir. Preferably, ganciclovir is administered in a dose of from about 1–20 mg/day/kg body weight. Preferably, acyclovir is administered in a dose of from about 1–100 mg/day/kg body weight and FIAU is administered in a dose of from about 1–50 mg/day/kg body weight.

The following examples are offered by way of illustration and are not intended to limit the invention in any manner.

EXAMPLE 1

Construction of the adenoviral vector

The construction of recombinant adenoviral vectors containing the herpes simplex virus-thymidine kinase (HSV-TK) gene (Summers, W. C., et al. at PNAS 78(3), pp. 1441–1445 (1981)) is shown in FIG. 1. Three different vectors were constructed, each with a different promoter inserted 5' to the coding sequence and polyadenylation signal of the HSV-TK gene: (1) the long terminal repeat sequence of the Rous Sarcoma Virus (Ad/RSV-TK); (2) the early gene promoter of the cytomegalovirus (Ad/CMV-TK); and (3) the thymidine kinase gene promoter of herpes simplex virus (Ad/HSV-TK).

EXAMPLE 2

Transduction of C6 Glioma cell

Transduction of C6 glioma cells in vitro was accomplished using a recombinant adenoviral vector containing the bacterial B-galactosidase gene. $5 \times 10^5$ C6 cells were plated on 1.5 cm diameter wells and transduced with AdV/RSV-B-gal at various viral doses and stained with X-gal two days later. Panel A illustrates the results using an moi of O. Panel B shows the results using an moi of 125. Panel C illustrates the results using an moi of 500 and Panel D shows the results when an moi of 2,000 was used.

EXAMPLE 3

Transduction of C6 cells using the HSV-TK gene

Transduction of C6 glioma cells was also accomplished using a recombinant adenoviral vector containing the HSV-TK gene (Ad/RSV-TK). $5 \times 10^5$ C6 cells were plated on 1.5 cm diameter wells and transduced with the viral vector at different doses as indicated. Cells were harvested two days later and protein extracts prepared. The HSV-TK enzymatic activity was determined by phosphorylation of $^3$H-acyclovir as described in James, et al., *J. Biol. Chem.*, 253 (24):8721–8727 (1978).

Figure 3:
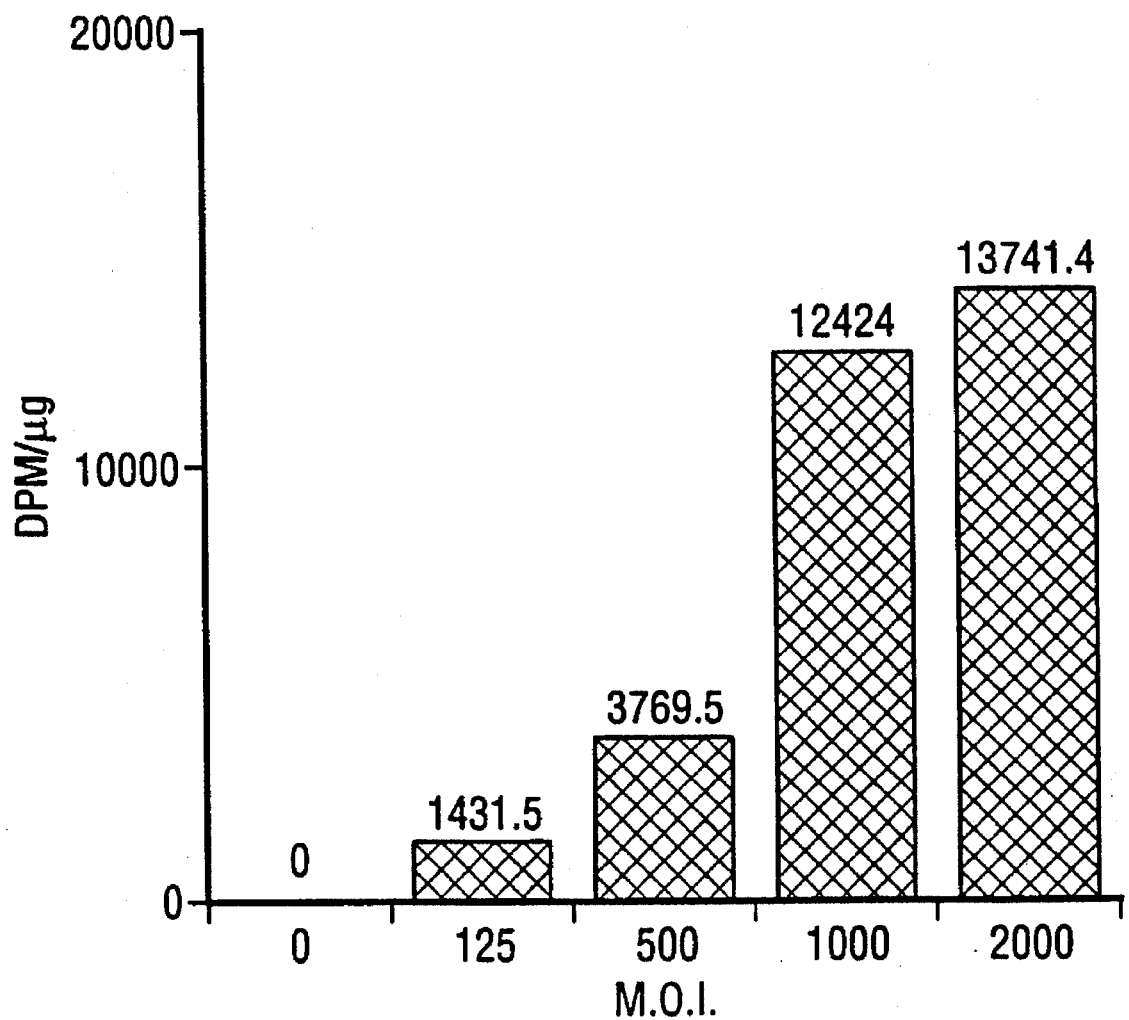
FIG. 3 shows HSV-TK enzymatic activity in C6 glioma cells after transduction with a recombinant adenoviral vector containing the HSV-TK gene.

As can be seen from FIG. 3, HSV-TK activity was highest in C6 cells after transduction with AD/RSV-TK having an m.o.i. of 1000 and 2000, respectively.

EXAMPLE 4

Ganciclovir susceptibility of HSV-TK+ C6 cells

Figure 4:
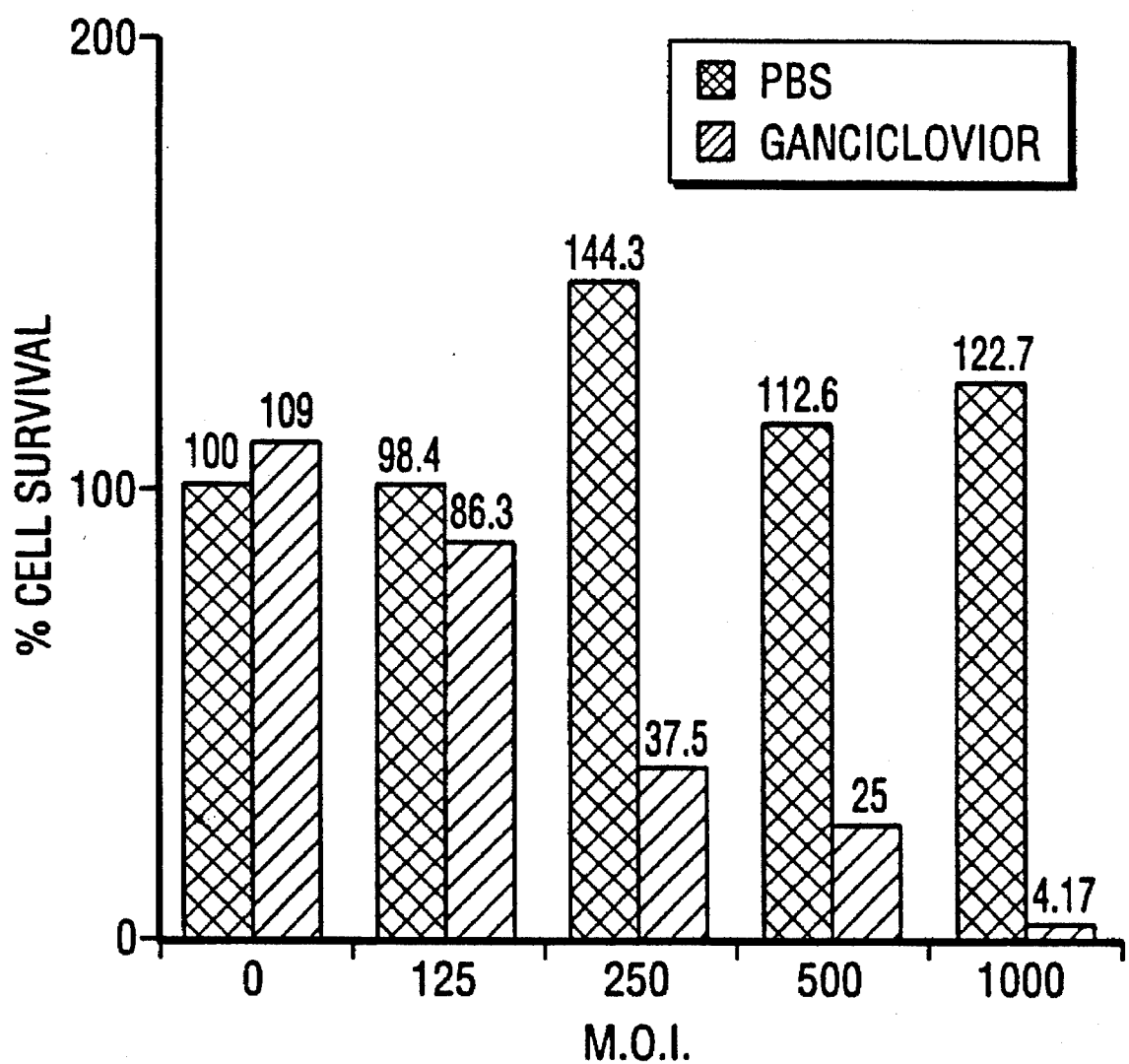
FIG. 4 shows the susceptibility to ganciclovir toxicity of Ad/RSV-TK transduced C6 glioma cells in vitro.

The susceptibility to ganciclovir toxicity of Ad/RSV-TK transduced C6 glioma cells is shown in FIG. 4. Duplicate plates of viral transduced cells in FIG. 3 were subjected to ganciclovir treatment at 2 ug/ml and the number of survival cells was counted at 72 hours.

FIG. 4 illustrates the effect of ganciclovir in C6 cells after transduction with AD/RSV-TK. FIG. 4 shows that an m.o.i. of 250 produced a cell kill of 62.5%; and m.o.i. of 500 resulted in a cell kill of 75%. Most dramatically, an m.o.i. of 1000 resulted in a cell kill of approximately 95%.

EXAMPLE 5

Gene therapy strategy

Figure 5:
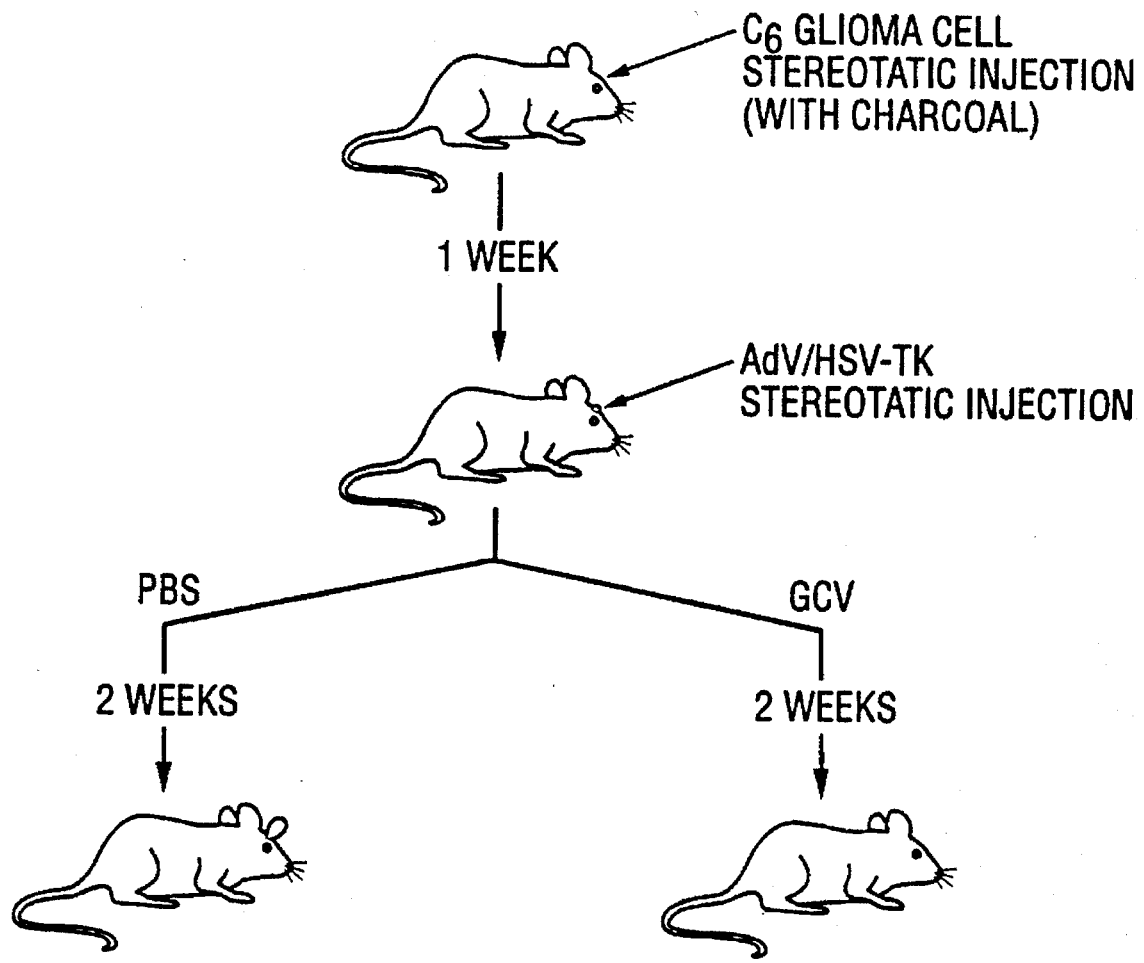
FIG. 5 shows the strategy for gene therapy of brain tumors using recombinant adenoviral vectors containing HSV-TK.
Figure 6:
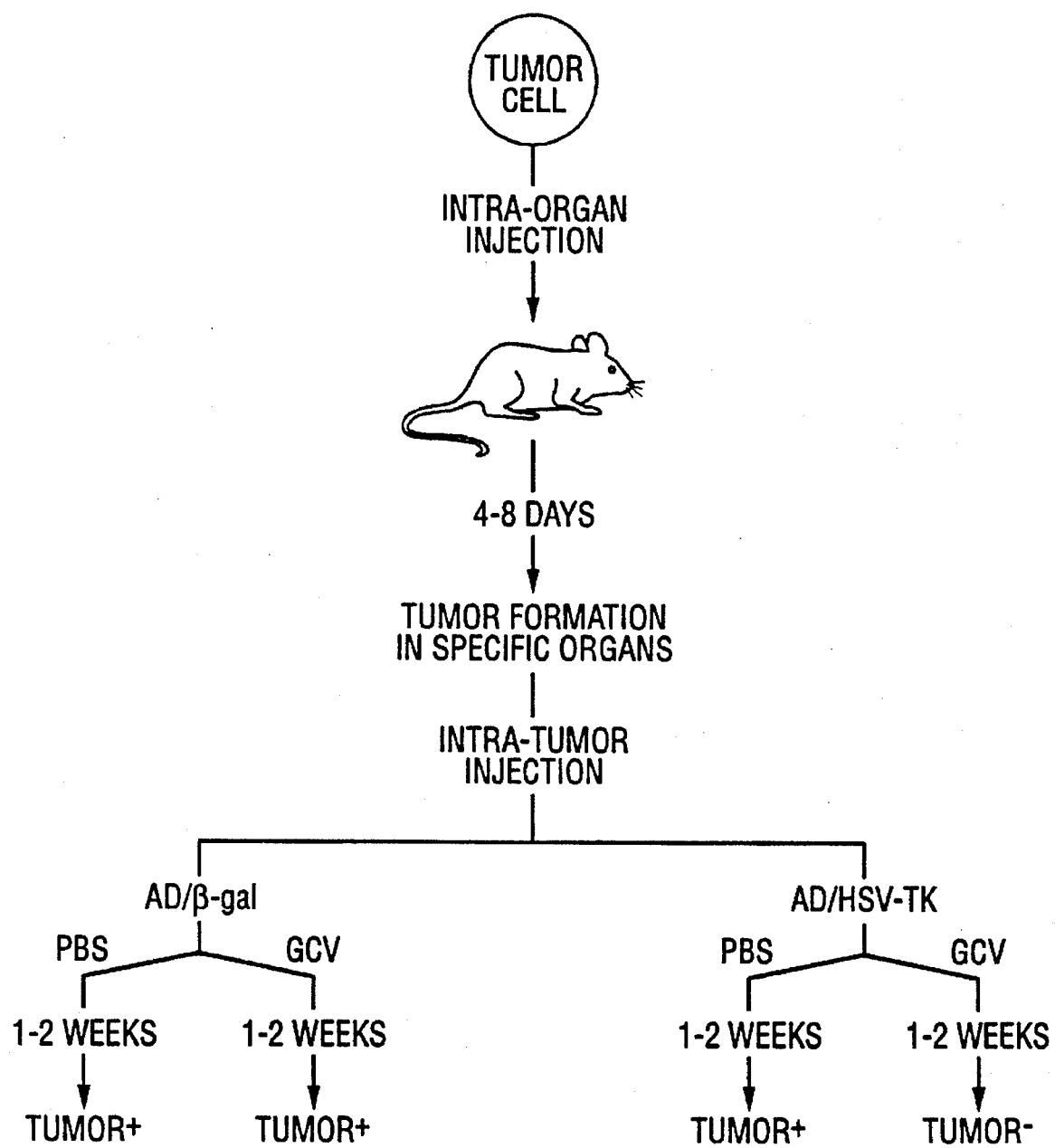
FIG. 6 shows a strategy for gene therapy of a generic solid tumor.

The strategy for gene therapy of brain cancer using recombinant adenoviral vectors containing HSV-TK is shown in FIGS. 5 and 6. In FIG. 5, C6 glioma cells were injected stereotactically into nude mouse brain with a little charcoal to mark the site of injection. About 1 week later, Ad/RSV-TK was injected into the tumor stereotactically. The mice were then divided into 2 groups, one treated with ganciclovir for 6 days and the other with phosphate-buffered saline (PBS). The animals were then kept without further treatment until tumors developed, i.e., about one to two weeks.

FIG. 6 shows intra-organ injections of tumor cells into mice. After 4–8 days, the mice were divided into two groups. In one group AD/βD-gal was injected into the tumor and in the other group AD/HSV-TK was injected into the tumor. After about 1–2 weeks, half the mice in each group were treated with PBS and the other half were treated with ganciclovir. Only the mice treated with ganciclovir and AD/HSV-TK showed tumor regression.

EXAMPLE 6

Effect of Ad/RSV-TK injection and Ganciclovir on brain tumors

Experimental animals were inoculated with 10⁴ C6 glioma cells by stereotactic injection into the brain. After 4–8 days, 3×10⁸ particles of recombinant adenoviral vector containing the HSV-TK (Ad/RSV-TK) gene were stereotactically injected into the same site. Twelve hours later, the animals were either treated i.p. daily with buffer (PBS) or Ganciclovir (GCV:125 mg/kg) for 6 consecutive days. The animals were kept without further treatment until the 20th day from the day of tumor cell inoculation and the appearance of brain tumors for individual animals was recorded.

Figure 7:
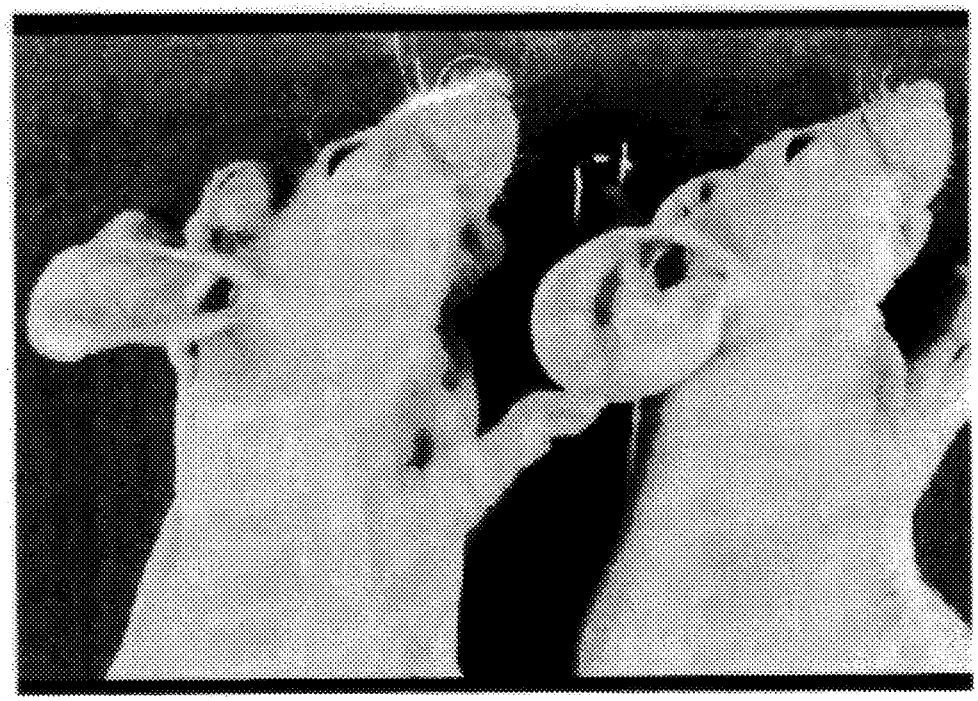
FIG. 7 shows experimental animals at 20 days post C6 Glioma cell inoculation into the brain, followed by stereotactic Ad/RSV-TK administration. The left animal was treated with PBS and the right animal treated with ganciclovir.

FIG. 7 shows experimental animals at 20 days post C6 glioma cell inoculation into the brain followed by stereotactic Ad/RSV-TK administration. A representative PBS-treated animal with obvious brain tumor is shown on the left panel of FIG. 7 and a representative GCV-treated mouse without obvious brain tumor is shown on the right panel of FIG. 7.

EXAMPLE 7

Gross anatomy of mouse brains with and without tumor

Figure 8:
FIG. 8 shows whole brain of mice as described in FIG. 7 after either PBS treatment (left) or ganciclovir treatment (right).

FIG. 8 shows whole brains of mice after either PBS treatment (left) or ganciclovir treatment (right) as described in Example 6. The brains were obtained from experimental animals at 20 days after tumor cells inoculation as described above. The tumor mass in PBS treated mice was dissected from the brain and placed on top of the organ. Furthermore, because the C6 glioma cells were originally injected into mouse brain with a little charcoal, the ganciclovir treated mouse brain has a spec of charcoal which demonstrates the site of tumor cell injection.

TABLE I

Brain Tumor Treatment with an Adenoviral Vector having the HSV-TK Gene

| TREATMENT | PBS | GCV |
| --- | --- | --- |
| Number of Treated Animals | 4 | 4 |
| Number of Animals with Brain Tumor | 4 | 1 |

EXAMPLE 8

Effect of ganciclovir on a breast cancer cell line

The "by-stander" effect in solid tumors was examined using a breast cancer cell line (MOD) derived from BALB/c mouse. This cell line easily forms localized tumors by subcutaneous injection of tumor cells into congenic recipients. Thus, this cell line can be used as a model for gene therapy for breast cancer.

Figure 9:
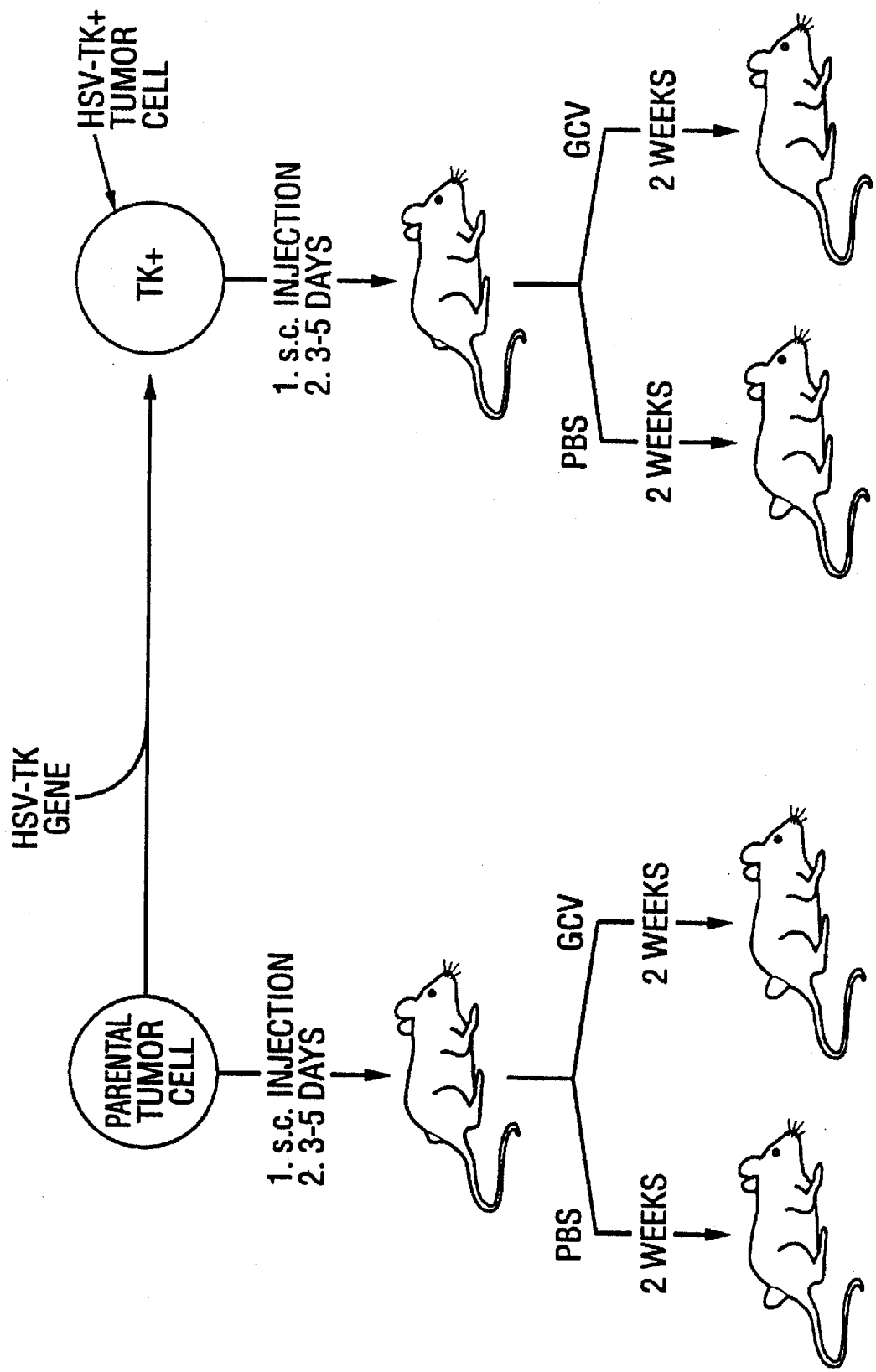
FIG. 9 shows a schematic of the effect of ganciclovir treatment and HSV-TK$^+$ breast tumor (MOD) regression.

FIG. 9 is a schematic of the effect of ganciclovir treatment and HSV-TK+ tumor regression. FIG. 9 shows that, in one case, the parental tumor cells were injected subcutaneously in mice. The mice were divided into two groups. One group was treated with PBS; the other group was treated with GCV for 5 days. Two weeks later, the animals were sacrificed. FIG. also shows that another group of mice were injected with tumor cells into which the HSV-TK gene was inserted in vitro (HSV-TK+). Subsequently, the mice were treated with either PBS or GCV as described above.

Figure 10A:
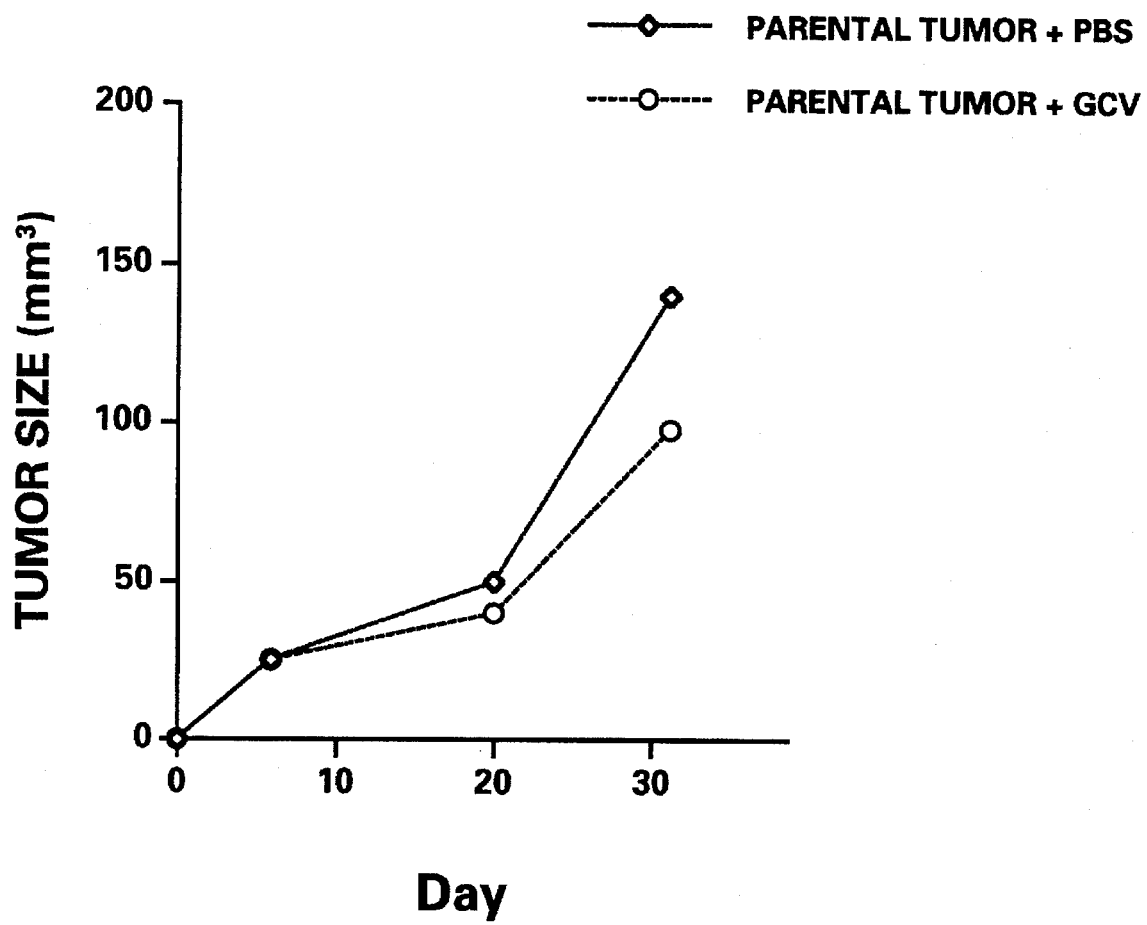
FIG. 10 shows the effect of ganciclovir treatment on HSV-TK$^+$ breast tumor (MOD) size.
Figure 10B:
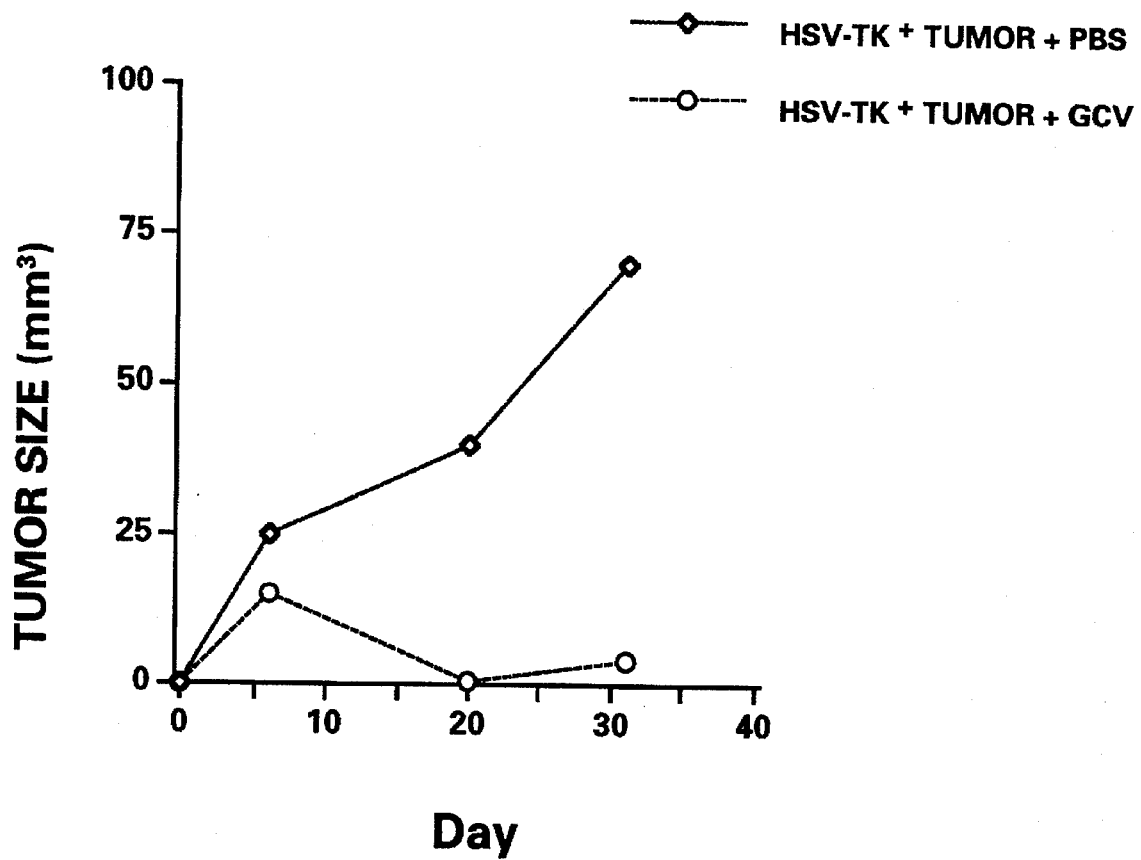

FIG. 10 shows the effect of ganciclovir treatment on tumor size. The top panel shows that there was little significant difference between treatment with PBS or GCV in mice injected with the parental cells alone. The bottom panel of FIG. 10 shows that ganciclovir treatment significantly reduced tumor size when the HSV-TK gene had been inserted into the tumor cells prior to injection into the mice.

Figure 11:
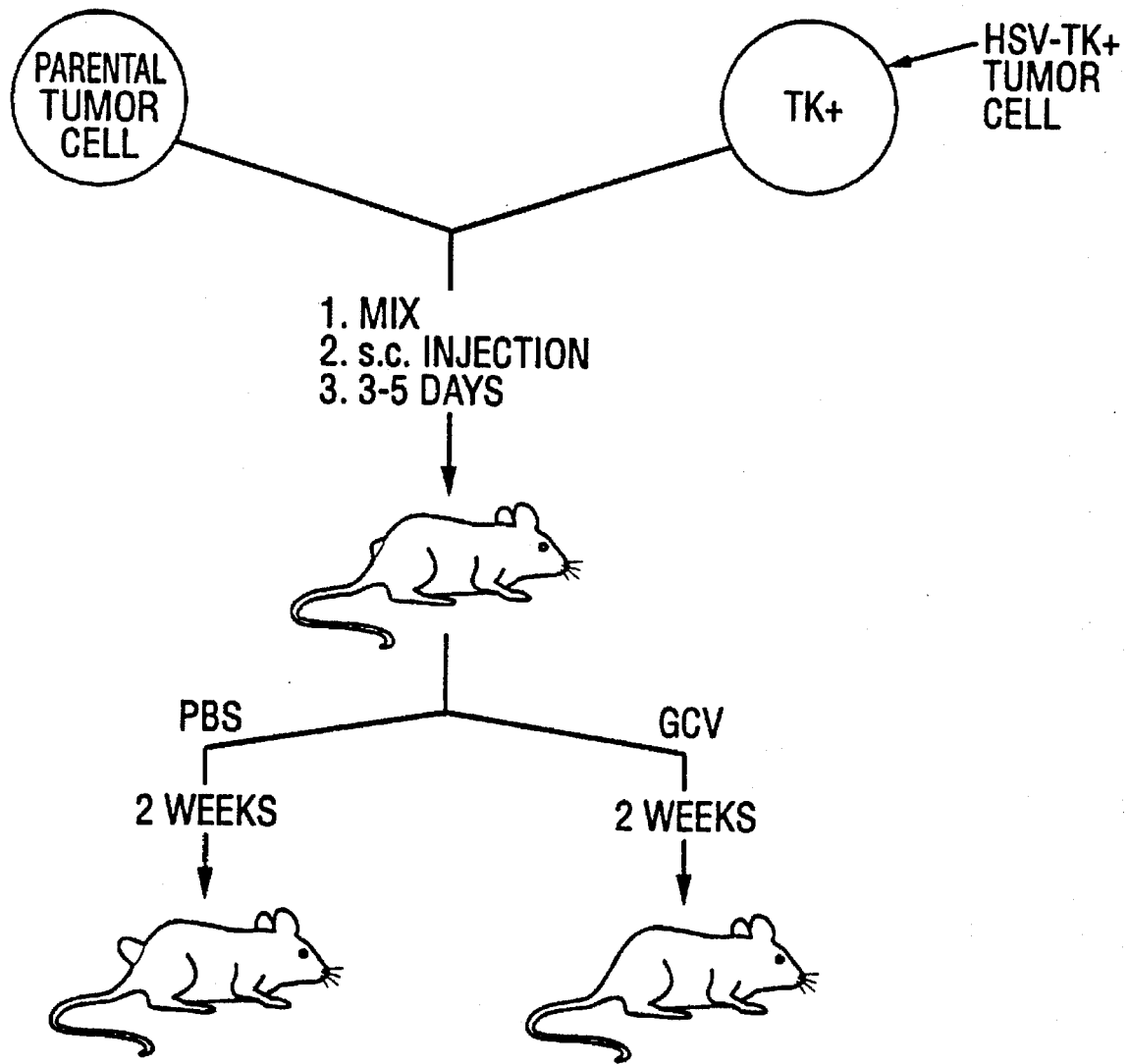
FIG. 11 shows a schematic of the bystander effect when parental breast tumor (MOD) cells and tumor cells containing the HSV-TK gene were mixed and injected subcutaneously into mice.

FIG. 11 shows a schematic of the bystander effect. In the schematic of FIG. 11, parental tumor cells and tumor cell containing the HSV-TK gene were mixed and injected subcutaneously into mice. The mice were then treated with either PBS or GCV.

Figure 12:
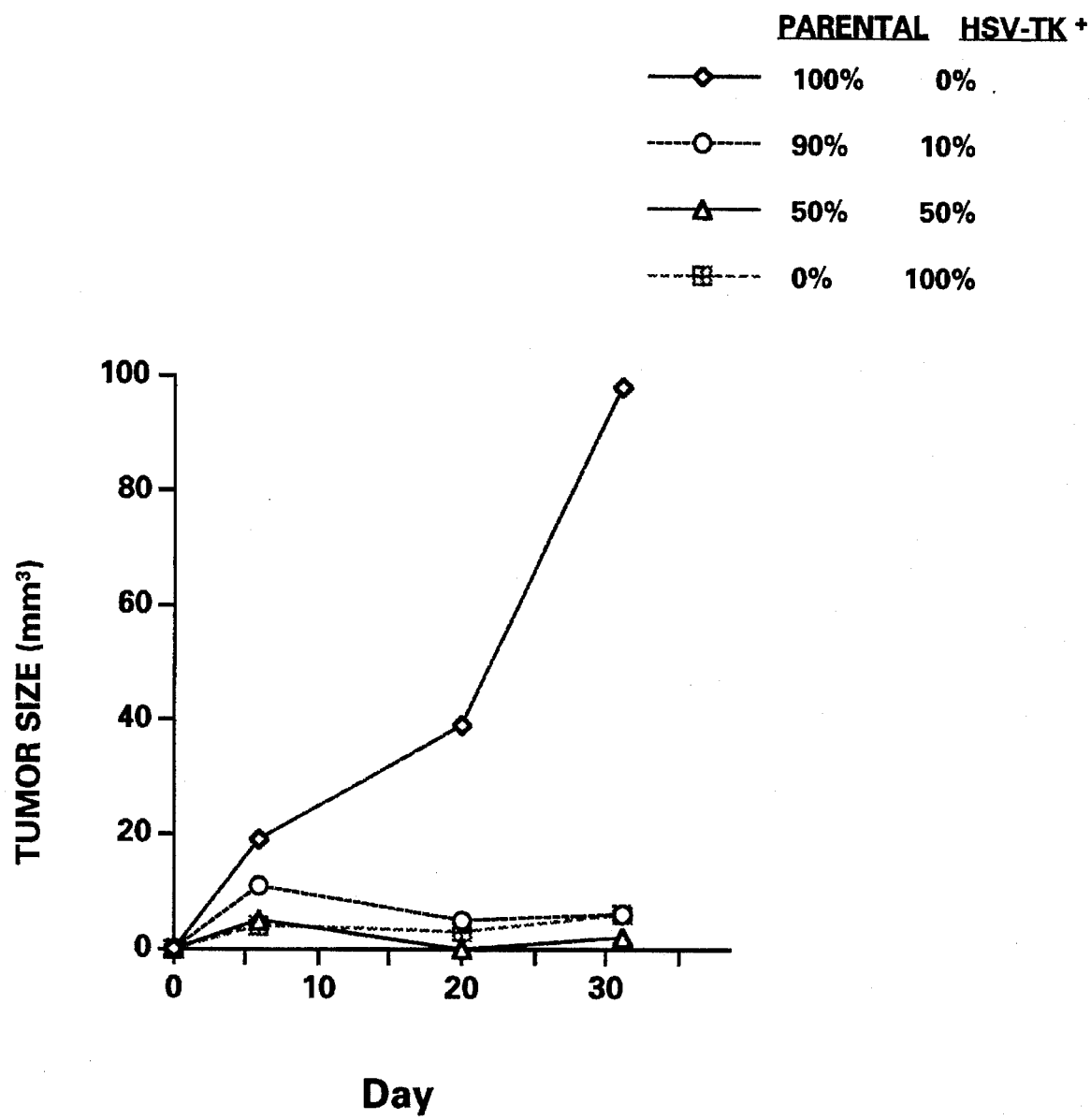
FIG. 12 shows the effect of PBS or ganciclovir on tumor size when mice had been treated with either 100% parental tumor cells, 100% HSV-TK containing tumor cells, 90% parental/10% HSV-TK tumor cells or 50% parental/50% HSV-TK breast tumor (MOD) cells.

HSV-TK gene transformed MOD cells in vitro exhibited greatly enhanced sensitivity to the toxic effects of ganciclovir over the parental tumor cells. When tested in vivo, not only the growth of HSV-TK gene transformed MOD cells were inhibited by intraperitoneal administration of ganciclovir but the sold tumors also regressed in mice. Regression, however, was not observed with tumors derived purely from the parental tumor cells. More importantly, a strong "by-stander" effect in the breast tumor cells in vivo was also observed. When animals were co-injected with the HSV-TK expressing MOD cells and the parental tumor cells, as few as 10% of HSV-TK expressing cells was sufficient to inhibit overall tumor growth in the animals after ganciclovir treatment (FIG. 12). In this set of animals however, the tumors recurred after 30–45 days. On the other hand, animals inoculated with 90% or 50% TK+ cells remained tumor free during this period.

Cell-type specificity of HSV-TK gene expression after recombinant adenoviral vector administration in a particular solid tumor, papilloma or wart can also be achieved with the use of tissue-specific promoters to direct the transcription of the HSV-TK gene. Some examples of the various tissue specific promoters are shown in Table II.

TABLE II

| TUMOR | PROMOTERS |
|---|---|
| liver | albumin, alpha-fetoprotein, $\alpha_1$-antitrypsin, transferrin transthyretin |
| colon | carbonic anhydrase I |
| ovary, placenta | estrogen, aromatase cytochrome P450, cholesterol side chain cleavage P450, 17 alpha-hydroxylase P450 |
| prostate | prostate specific antigen, gp91-phox gene, prostate-specific kallikrein (hKLK2) |
| breast, G.I. | erb-B2, erb-B3, β-casein, β-lactoglobulin, WAB (whey acidic protein) |
| lung | surfactant protein C Uroglobin (cc-10, CIIacell 10 kd protein) |
| skin | K-14-keratin, human keratin 1 or 6, loicrin |
| brain | glial fibrillary acidic protein, mature astrocyte specific protein, myelin, tyrosine hydroxylase |
| pancreas | villin, glucagon, Insulin Islet amyloid polypeptide (amylin) |
| thyroid | thyroglobulin, calcitonin |
| bone | Alpha 1 (I) collagen, osteocalcin, bone sialoglycoprotein |
| kidney | renin, liver/bone/kidney alkaline phosphatase, erythropoietin (epo) |

All patents and publications mentioned in this specification are indicative of the levels of those skilled in the art to which the invention pertains. All patents and publications are herein incorporated by reference to the same extent as if each individual publication is specifically and individually indicated to be incorporated by reference.

One skilled in the art will readily appreciate that the present invention is well adapted to carry out the objects and obtain the ends and advantages mentioned, as well as those inherent therein. The methods, procedures, treatments, molecules, and specific compounds described herein are presently representative of preferred embodiments, are exemplary and are not intended as limitations on the scope of the invention. Changes therein and other uses will occur to those skilled in the art which are encompassed within the spirit of the invention and are defined by the scope within the claims.

What we claim is:

1. A method of causing regression of a solid tumor in a mammal comprising the steps of, introducing an adenoviral vector directly into said tumor wherein said vector is comprised of a DNA sequence encoding HSV-tk operatively linked to a promoter and wherein said tumor express HSV-tk; and administering ganciclovir, acyclovir or FIAU in amounts sufficient to cause regression of said tumor when said ganciclovir, acyclovir or FIAU is converted to a toxic compound by HSV-tk.

2. A method of causing regression of a solid tumor in a mammal comprising the steps of, introducing an adenoviral vector directly into said tumor wherein said vector is comprised of a DNA sequence encoding VZV-tk operatively linked to a promoter and wherein said tumor express VZV-tk; and administering ganciclovir, acyclovir, FIAU or 6-methoxypurine arabinoside in amounts sufficient to cause regression of said tumor when said ganciclovir, acyclovir, FIAU or 6-methoxypurine arabinoside is converted to a toxic compound by VZV-tk.

3. The method of claim 1, wherein said ganciclovir is administered in a dose of from about 1 mg/day/kg to about 20 mg/day/kg body weight.

4. The method of claim 1, wherein said acyclovir is administered in a dose of from about 1 mg/day/kg to about 100 mg/day/kg body weight.

5. The method of claim 1 wherein said FIAU is administered in a dose of from about 1 mg/day/kg to about 50 mg/day/kg.

6. The method of claim 1 or 2 wherein said promoter is selected from the group consisting of Rous sarcoma virus long terminal repeat, cytomegalovirus promoter, murine leukemic virus—long terminal repeat, simian virus 40 early and late, and herpes simplex virus—thymidine kinase promoter.

* * * * *